United States Patent
Stieven

(10) Patent No.: US 9,962,239 B2
(45) Date of Patent: May 8, 2018

(54) ELASTIC RING MOUNTING PISTOL AND MAGAZINE

(71) Applicant: Peter Stieven, Schorndorf (DE)

(72) Inventor: Peter Stieven, Schorndorf (DE)

( * ) Notice: Subject to any disclaimer, the term of this patent is extended or adjusted under 35 U.S.C. 154(b) by 0 days. days.

(21) Appl. No.: 15/668,491

(22) Filed: Aug. 3, 2017

(65) Prior Publication Data

US 2017/0367794 A1    Dec. 28, 2017

Related U.S. Application Data

(63) Continuation-in-part of application No. 12/998,592, filed on Mar. 9, 2012, now abandoned.

(51) Int. Cl.
*A61C 3/00* (2006.01)
*A61C 7/30* (2006.01)

(52) U.S. Cl.
CPC .................................. *A61C 7/306* (2013.01)

(58) Field of Classification Search
CPC .. A61C 7/306; A61C 7/30; A61C 7/00; A61C 3/00

USPC ............. 433/3; 81/434, 433, 57.1, 435, 431; 227/8

See application file for complete search history.

(56) References Cited

U.S. PATENT DOCUMENTS

2005/0221247 A1* 10/2005 Quillian ................. A61C 7/306
433/3

* cited by examiner

*Primary Examiner* — Cris L Rodriguez
*Assistant Examiner* — Mirayda A Aponte
(74) *Attorney, Agent, or Firm* — Klaus J. Bach

(57) ABSTRACT

An elastic mounting ring installation tool for connecting braces to brackets attached to the teeth of a patient has a housing with a barrel section, at the front end of which a magazine holder with a magazine provided with elastic rings for placement onto brackets provided on the teeth is arranged for mounting the braces to the teeth by the elastic mounting rings and a rod with wire fingers is movably supported in the barrel section for scooping up the elastic rings and transferring them to tooth brackets of the patient. The magazine holder is supported so as to be movable away from the wire fingers in a direction normal to the axis of the rod for pulling an elastic ring engaged by the wire fingers in a sideward direction for disconnecting the elastic ring from the magazine.

6 Claims, 1 Drawing Sheet

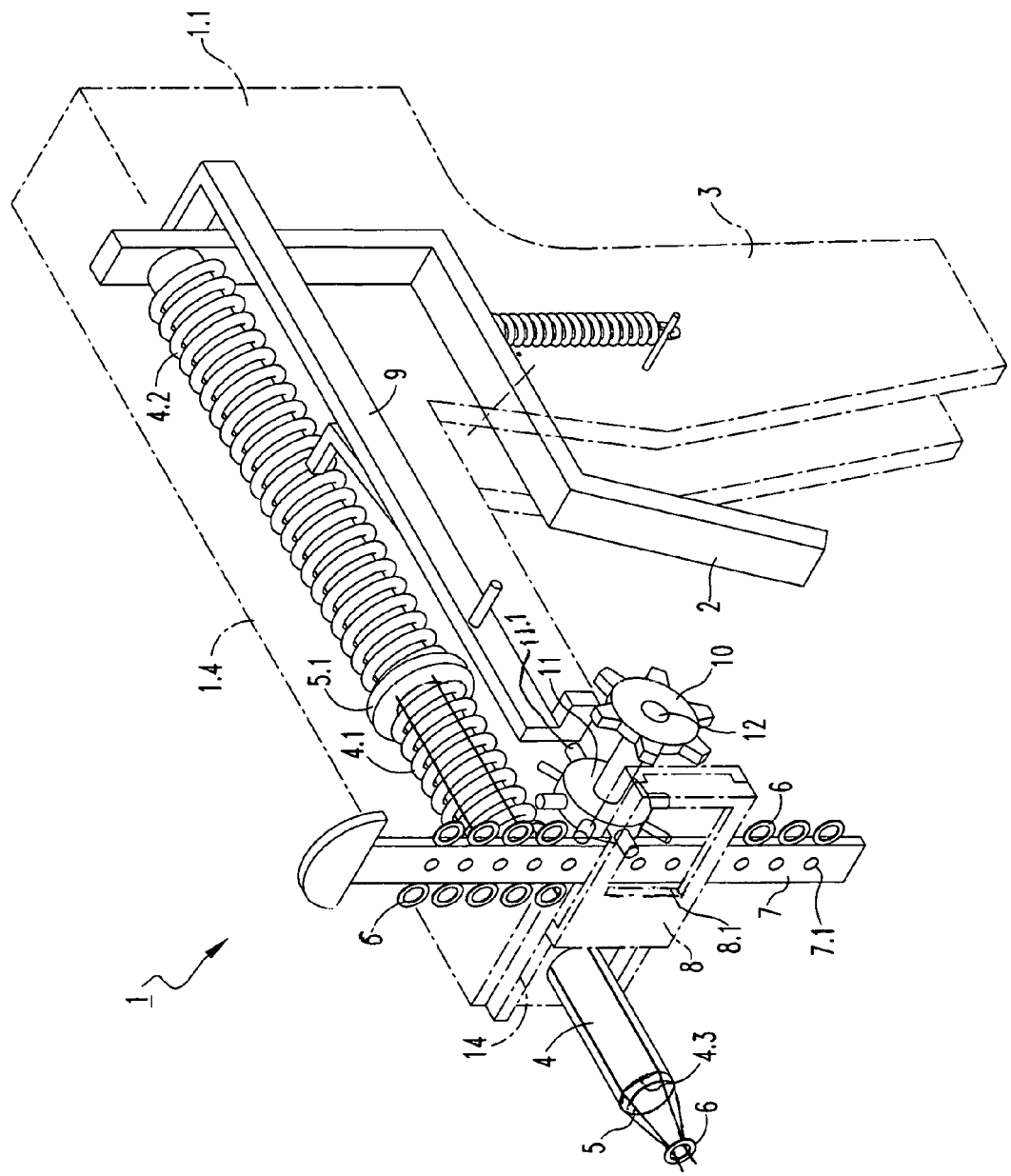

ELASTIC RING MOUNTING PISTOL AND MAGAZINE

This is a Continuation-In-Part application of U.S. patent application Ser. No. 12/998,592 filed Mar. 9, 2012, claiming the priority of international patent application PCT/DE2003000983 filed Jul. 22, 2009.

BACKGROUND OF THE INVENTION

The present invention resides in an elastic ring installation tool for the installation of elastic rings on brackets attached to the teeth of a patient for mounting orthodontic fixtures such as braces to the teeth of the patient. The elastic rings are attached onto a holder in the form of for example a magazine including a strip which is movably supported by a support member and are taken up one after another by an engagement device for installation of the orthodontic fixture.

Tools of this type are generally known. Such a so-called ligature dispenser instrument in the form of a pistol is for example shown in U.S. Pat. No. 7,220,121 B2. In this instrument, the ligatures or elastic rings are supported on the circumference of a circular support disc which is disposed rotatably in a cassette and from which the rings are picked up by a tubular carrier with wire-like fingers which are advanced to enter an elastic ring and take it along to pull it off the circular support disc while the fingers and, together therewith, an elastic ring is moved forward. As a result, the ring pulled off the support disc is disoriented from its position in a plane normal to the advancing wire-like fingers on which it is supported while an attachment neck by way of which the elastic ring is attached to the support disc is stretched in the axial direction of the tubular carrier. When the attachment neck finally rips, the elastic ring is no longer oriented in a plane normal to the extension of the tubular carrier as its needed for a proper installation.

It is the principal object of the present invention to provide an elastic ring installation tool with a magazine in the form of a holder for elastic mounting rings and an operating mechanism by which the elastic mounting rings are securely engaged and removed from the holder while safely remaining held by the support fingers of the ring installation tool in their desired orientation for installation on attachment brackets provided on the teeth of a patient.

SUMMARY OF THE INVENTION

In an elastic ring installation tool for connecting braces to brackets attached to the teeth of a patient, the tool comprising a housing with a barrel section at the front end of which a magazine in the form of a support strip provided with elastic rings for placement onto the brackets to attach the braces to the teeth of the patient is arranged, an operating rod with wire fingers is movably supported in the barrel section for picking up an elastic ring in front of which a support wall portion of a magazine holder is disposed to hold the elastic ring while the wire fingers are moved into the ring, the magazine is supported by the magazine holder which is movable in a direction normal to the axis of the pick-up rod for pulling an elastic ring engaged by the wire fingers sidewardly away from the wire fingers so as to remove the elastic ring from the support strip and transferring it to a tooth bracket. To this end the operating rod is moved forward to spread the fingers apart and widen the elastic ring for placing it onto a tooth bracket.

The invention will become more readily apparent from the following description of an exemplary embodiment thereof with reference to the accompanying schematic drawings.

BRIEF DESCRIPTION OF THE DRAWINGS

FIG. 1 shows schematically an elastic ring installation tool according to the invention.

DESCRIPTION OF AN EXEMPLARY EMBODIMENT OF THE ELASTIC RING INSTALLATION TOOL

The elastic ring installation tool according to the present invention as schematically shown in the drawing is preferably in the form of a pistol 1 with a housing 1.1 including a grip section 3 with a trigger 2 pivotally supported in the housing 1.1. The housing 1.1 further has a barrel section 1.4 provided with a magazine holder 8 supported at the front end of the barrel section 1.4 so as to be movable sidewardly. As shown in FIG. 1 the magazine holder 8 is slidably supported by tracks 14 so that it is movable sidewardly between two opposite end positions. The magazine holder 8 includes a passage 8.1 for accommodating an elastic ring magazine in the form of a strip 7 provided with elastic mounting rings 6 attached to the ring strip 7 by small rip-off necks or areas. The ring strip 7 is provided with engagement holes 7.1 and the magazine holder 8 includes a transport wheel 11 with pins 11.1 engaging in openings 7.1 in the ring strip 7 for moving the ring strip 7 through the magazine holder 8. The transport wheel 11 is mounted onto a shaft 12 which is rotatably supported by the magazine holder and carries at its end opposite the transport wheel 11 a drive gear 10. The drive gear 10 is actuated by an actuating rod 9 for advancing the drive gear 10 by a step each time the trigger 2 is released (marked only schematically) and, at the same time, advancing the magazine ring strip 7 for moving another elastic mounting ring 6 into a position to be picked up.

In the barrel section 1.4, an operating rod 4 is axially movably supported biased by springs 4.1 and 4.2 into a retracted position. The operating rod 4 is movable forward to an extended position as shown in FIG. 1. The operating rod 4 carries engagement wires 5 which may actually be disposed in axial grooves formed in the operating rod 4. The engagement wires 5 are connected at their rear ends to a support sleeve or ring 5.1, which is axially movably supported on the operating rod 4. At their front ends, the engagement wires 5 converge conically and jointly form a finger structure for entering a ring 6 supported by the ring strip 7—as shown FIG. 1—upon forward movement of the operating rod 4 together with the support ring 5.1 and the engagement wires 5.

Upon forward movement of the operating rod 4 and the engagement wires 5, the conical front end structure 4.3 of the operating rod 4 forming a ramp area moves the magazine holder 8 to the side, thereby disconnecting the scooped-up elastic ring 6 from the ring strip 7 by a sideward pulling force so that the operating rod 4 with the engagement wires 5 and the ring 6 scooped up by the engagement wires 5 can move further forward. At that point, the operating rod 4 is further advanced while the support ring 5.1 and the engagement wires 5 are retained by a stop so that the operating rod front end structure 4.3 moves into the conical area at the front of the engagement wires and forces the engagement wires 5 apart. As a result, the elastic ring is expanded and can be placed over a bracket structure for connecting a brace to the teeth of a patient. Upon retraction of the operating rod 4 out of the conical wire section, the wire fingers return and release the elastic ring which remains attached to the patient's teeth so as to retain the tooth brace in position. When the operating rod 4 is again returned to its retracted position, the magazine can again slide back to its position in front of the operating rod 4 and, actuated by the transport lever 9, the gear wheel 10 and, together therewith, the pin wheel 11 is rotated so as to move the ring strip 7 by a step for placing the next elastic ring into a position to be picked up by the engagement wires 5. In this way now the next elastic ring 6 can be installed by again advancing the rod 4 when the trigger lever 2 is again pressed.

It is noted that the magazine holder 8 is biased into a position in front of the operating rod 4 and the engagement wires 5 for example by a spring which is not shown. However, other movement mechanisms may be provided for moving the magazine holder from or to its rest position in front of the operating rod 4. Instead of the ramp structure for moving the magazine holder to the side, for example a lever mechanism may be used or an electric motor or a spring motor may be employed and either one may be activated for example by a switch or other trigger to initiate the sideward movement of the magazine holder.

The invention also resides in a magazine in the form of a ring holder comprising a center strip to the sides of which the elastic mounting rings 6 are attached in such a way that they can be easily removed. The strip itself is provided with center holes for engagement by the pins of the transport wheel 11 of the installation tool as described above.

Furthermore, the invention is concerned with a method for removing elastic rings from the elastic ring magazine for attachment to brackets mounted to the teeth of a patient utilizing an installation tool in such a way that the elastic rings can easily be properly applied to the tooth brackets.

Generally, in prior art procedures the elastic mounting rings are pulled from a ring holder by an installation tool by forward movement of a ring engagement structure whereby the rings are held back by their attachment to the ring holder until they are ripped off. At that point however the rings are, and remain, in a tilted orientation which negatively affects the installation accuracy.

In accordance with the method according to the present invention, the rings are pulled off a ring holder by a sideward motion of the ring magazine holder away from the elastic ring magazine. They remain therefore oriented in a plane normal to the movement direction of the ring engagement structure thereby facilitating proper installation of the elastic rings onto the tooth brackets attached to the teeth of a patient for mounting a tooth prosthesis.

What is claimed is:

1. An elastic mounting ring installation tool (1) for connecting braces to brackets attached to teeth of a patient for the installation of orthodontic braces, the installation tool comprising: a housing (1.1) with a barrel section (1.4) having a front end; an operating rod (4) axially movably supported in the barrel section (1.4) so as to be extendable through a front end of the barrel section (1.4); a magazine holder (8) supported at the front end of the barrel section (12) so as to be movable in a plane normal to the extension of the operating rod (4), the magazine holder (8) supporting an elastic mounting ring magazine (7) having elastic mounting rings (6) attached thereto and being position-adjustable to a location where one of the elastic mounting rings (6) is in axial alignment with the operating rod (4), the operating rod (4) being provided with elastic mounting ring engagement wire fingers (5) extending into the elastic ring upon advancement of the operating rod (4), and an actuating structure for moving the magazine holder (8) together with the elastic mounting ring magazine (7) and the elastic mounting rings (6) sideways for dislodging the elastic mounting ring (6) engaged by the elastic mounting ring engagement wire fingers (5) from the elastic mounting ring magazine (7), and the elastic mounting ring engagement wire fingers (5) being spreadable apart by the operating rod (11) so as to expand the elastic mounting ring (6) for placement thereof onto and around a tooth bracket attached to a tooth of the patient.

2. The elastic mounting ring installation tool as claimed in claim 1, wherein the magazine holder (8) is supported at the front end of the barrel section (1.4) by a slide structure so as to be slidable in a plane normal to the extension of the operating rod (4) and the elastic ring engagement wire fingers (5) are disposed on the operating rod (4) forming a conical front end area so as to jointly form at their front end an elastic mounting ring (6) support structure for scooping up an elastic mounting ring (6) and holding the elastic B mounting ring (6) while the magazine holder (8) is moved sideways for the removal of the elastic mounting ring from the elastic mounting ring magazine (7).

3. The elastic mounting ring installation tool as claimed in claim 2, wherein the operating rod (4) and the engagement wire fingers (5) have a conically converging front end area (4.3) and the elastic ring mounting engagement wire fingers (5) are connected at their rear ends opposite the conically converging front end areas (4.3) to a support ring (5.1) which is axially movably supported on the operating rod (4) and the operating rod (4) is provided with an inclined ramp area (4.3) for moving the magazine holder sidewardly when the operating rod is advanced and also for spreading the wire fingers to expand the elastic mounting ring (6).

4. The elastic mounting ring installation tool as claimed in claim 1, wherein the elastic mounting ring magazine (7) comprises a strip with rings (6) attached thereto so as to project therefrom at opposite sides of the strip and the strip is provided with openings (7.1) engaged by a transport wheel (11) for moving the elastic mounting ring magazine (7) through the magazine holder (8).

5. An elastic mounting ring magazine for use in an elastic mounting ring installation tool as claimed in claim 1, comprising: a strip with elastic mounting rings (6) attached thereto so as to project therefrom at opposite sides of the strip, the strip being further provided with spaced openings (7.1) for engagement by a transport wheel (11) of the elastic mounting ring installation tool.

6. A method of installing elastic mounting rings onto brackets attached to teeth of a patient for connecting orthodontic braces to the teeth, comprising the steps of:

removing an elastic mounting ring from an elastic mounting ring holder, to which elastic mounting rings are connected, by scooping up one of the elastic mounting rings by an expandable engagement structure and expanding the scooped-up elastic mounting ring and moving it forward for depositing it on a bracket attached to a tooth of the patient, wherein, for disconnecting the elastic mounting ring from the elastic mounting ring holder, the elastic mounting ring holder is moved sidewardly in a plane normal to the direction of movement of the expandable engagement structure away from the elastic mounting ring scooped up so as to maintain the orientation of the elastic mounting ring on the expandable engagement structure in order to facilitate proper installation of the elastic mounting ring onto a tooth bracket.

\* \* \* \* \*